(12) United States Patent
Tohata et al.

(10) Patent No.: US 7,563,611 B2
(45) Date of Patent: Jul. 21, 2009

(54) RECOMBINANT MICROORGANISM

(75) Inventors: Masatoshi Tohata, Tochigi (JP);
Kazuhisa Sawada, Tochigi (JP);
Katsuya Ozaki, Tochigi (JP); Junichi Sekiguchi, Udea (JP)

(73) Assignee: Kao Corporation, Tokyo (JP)

( * ) Notice: Subject to any disclaimer, the term of this patent is extended or adjusted under 35 U.S.C. 154(b) by 195 days.

(21) Appl. No.: 10/578,615

(22) PCT Filed: Nov. 5, 2004

(86) PCT No.: PCT/JP2004/016890
§ 371 (c)(1),
(2), (4) Date: May 8, 2006

(87) PCT Pub. No.: WO2005/045045
PCT Pub. Date: May 19, 2005

(65) Prior Publication Data
US 2008/0081352 A1 Apr. 3, 2008

(30) Foreign Application Priority Data
Nov. 7, 2003 (JP) ............................. 2003-379114

(51) Int. Cl.
*C12N 1/20* (2006.01)
(52) U.S. Cl. .................................... 435/252.3; 435/325
(58) Field of Classification Search .............. 435/252.3, 435/325
See application file for complete search history.

(56) References Cited

FOREIGN PATENT DOCUMENTS

| WO | 96/34961 | 11/1996 |
|---|---|---|
| WO | 02/097064 | 12/2002 |

OTHER PUBLICATIONS

Yamamoto, Hiroki et al., "Determination of a 12 kb nucleotide sequence around the 76° region of the *Bacillus subtilis* chromosome", Microbiology, vol. 142, pp. 1417-1421, 1996.
Reizer, Jonathan et al., "Novel phosphotransferase system genes revealed by genome analysis—the complete complement of PTS proteins encoded within the genome of *Bacillus subtilis*", Microbiology, vol. 145, pp. 3419-3429, 1999.
Yamamoto, Hiroki et al., "Regulation of the glv Operon in *Bacillus subtilis*: YfiA (GlvR) Is a Positive Regulator of the Operon That is Repressed through CcpA and cre", Journal of Bacteriology, vol. 183, No. 17, 2001.
U.S. Appl. No. 10/578,613, filed May 8, 2006, Tohata et al.
U.S. Appl. No. 10/578,615, filed May 8, 2006, Tohata et al.

*Primary Examiner*—Karen Cochrane Carlson
(74) *Attorney, Agent, or Firm*—Oblon, Spivak, McClelland, Maier & Neustadt, P.C.

(57) ABSTRACT

The present invention provides a recombinant microorganism obtained by transferring, into a host microorganism which is capable of producing protein or polypeptide with increased productivity and which was identified by the present inventors, a gene encoding a protein or polypeptide, and a method for producing a protein or polypeptide by use of the recombinant microorganism.

36 Claims, 1 Drawing Sheet

RECOMBINANT MICROORGANISM

CROSS-REFERENCE TO RELATED APPLICATIONS

The present application is a National Stage (371) of PCT/JP04/16890, filed on Nov. 5, 2004, which claims priority to JP 2003-379114, filed on Nov. 7, 2003.

TECHNICAL FIELD

The present invention relates to a recombinant microorganism which may be used to produce useful proteins or polypeptides, as well as to such proteins and polypeptides.

TECHNICAL BACKGROUND

Microorganisms are widely used for industrially producing a broad range of useful substances, including alcoholic beverages, certain types of foods such as miso and shoyu, amino acids, organic acids, nucleic-acid-related substances, antibiotics, sugars, lipids, and proteins. These substances also find diversified uses, including foods, pharmaceuticals, detergents, products for daily use such as cosmetics, and a variety of chemical raw materials.

In industrial production of useful substances by use of microorganisms, improvement of productivity is one major topic of interest, and one approach therefor is breeding of microorganisms through mutagenesis-or other genetic means. Recently, in particular, with advancement of microbial genetics and biotechnology, more efficient breeding of useful microorganisms is performed through gene recombination techniques, and in association therewith, host microorganisms for obtaining recombinant genes are under development. For example, Bacillus subtilis Marburg No. 168, which has already been confirmed to be safe and have excellent characteristics as a host microorganism, has been further improved.

However, microorganisms inherently possess diversified genes so that they can cope with environmental changes in the natural world, and thus, they do not necessarily exhibit high production efficiency of proteins or similar substances in industrial production, where only limited production media are employed.

DISCLOSURE OF THE INVENTION

The present invention provides a recombinant microorganism prepared by transferring, to a mutant strain of microorganism from which at least one gene participating in membrane permeation of maltose (particularly either glvR or glvC) or one or more genes functionally equivalent to the gene have been deleted or knocked out, a gene encoding a heterologous protein or polypeptide.

MODES FOR CARRYING OUT THE INVENTION

Figure 1:
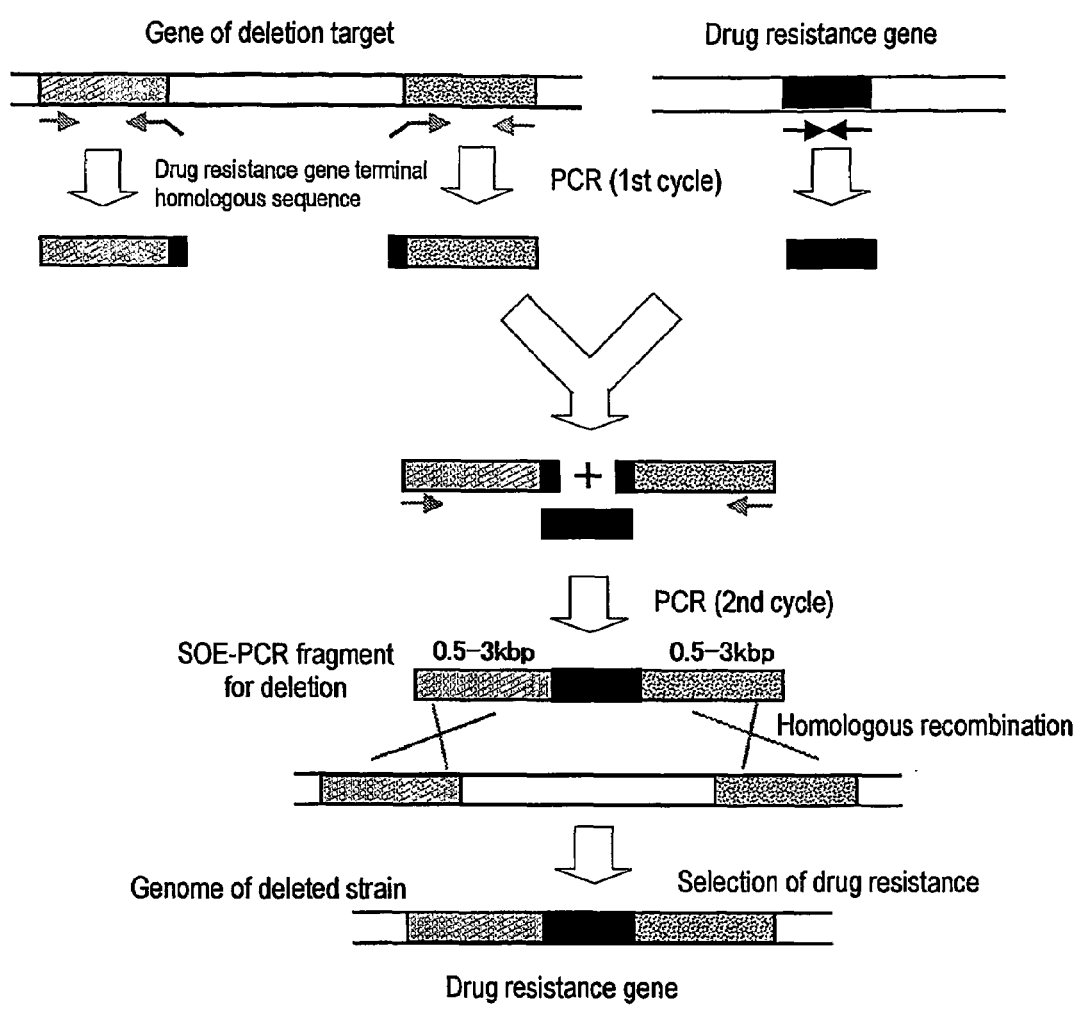
FIG. 1 schematically shows a method for preparing a DNA fragment for deleting a gene through SOE-PCR (SOE: splicing by overlap extension) (see Gene, 77, 61 (1989), and a method for deleting a target gene (replacing the target gene with a drug resistance gene) through use of the DNA.

The present invention is directed to a recombinant microorganism obtained by transferring, into a host microorganism which is capable of producing protein or polypeptide with increased productivity and which was identified by the present inventors, a gene encoding a protein or polypeptide, and to a method for producing a protein or polypeptide by use of the recombinant microorganism.

The present inventors have conducted extensive studies on, among many different genes encoded on the genome of a microorganism, genes which are not needed in or which are detrimental to the production of useful proteins or polypeptides, and surprisingly, have found that, when a gene encoding a target protein or polypeptide is transferred to a microorganism after a specific gene participating in membrane permeation of maltose employed as a predominant carbon source of a culture medium or a gene functionally equivalent to the gene is deleted or knocked out from the genome of the microorganism, productivity of the target protein or polypeptide is enhanced as compared with the case before the deletion or knocking out.

By use of the recombinant microorganism of the present invention, a target protein or polypeptide can be produced on a large scale with high efficiency.

In the present invention, homology between amino acid sequences and that between nucleic acid sequences are both determined by use of the Lipman-Pearson method (Science, 227, 1435 (1985)). Specifically, calculation is performed by use of a homology analysis program (Search Homology) developed by genetic information processing software, Genetyx-Win (Software Development Co., Ltd.), with ktup ( the unit size to be compared) being set 2.

No particular limitation is imposed on a parent microorganism for constructing the microorganism of the present invention, so long as it has a gene participating in membrane permeation of maltose. Specifically, any of the Bacillus subtilis genes or genes functionally equivalent thereto as shown in Table 1 may be employed. When cultur is performed by use of a medium containing maltose or maltooligo-saccharide as a primary carbon source, the microorganism is preferably of another class having a different maltose permeation system in which the mentioned gene does not participate. The gene may be of wild-type or a mutant. Specific examples include Bacillus subtilis and similar microorganisms belonging to the genus Bacillus, microorganisms belonging to the genus Clostridium, and yeast. Inter alia, microorganisms belonging to the genus Bacillus are preferred. In particular, Bacillus subtilis is preferred, from the viewpoint that complete genomic information of this microorganism has already been obtained, and thus genetic engineering techniques and genomic engineering techniques have been established, and that the microorganism has ability to secrete the produced protein extracellularly.

Examples of the target protein or polypeptide to be produced by use of the microorganism of the present invention include enzymes, physiologically active substances, and other proteins and polypeptides which find utility in foods, pharamceuticals, cosmetics, detergents, fiber treating agents, clinical assay agents, etc.

In the present invention, genes which are to be deleted or knocked out are those participating in membrane permeation of maltose. These genes are any of the Bacillus subtilis genes shown in Table 1, or are selected from among the genes functionally equivalent thereto.

The names, numbers, and functions of respective genes in the Tables contained herein conform with the Bacillus subtilis genome data reported in Nature, 390, 249-256 (1997) and made public by JAFAN (Japan Functional Analysis Network for Bacillus subtilis; BSORF DB) on the Internet.

TABLE 1

| Name of the gene | Gene ID | Functions or other information of the gene |
|---|---|---|
| glvC | BG11848 | PTS maltose-specific enzyme IICB |
| glvR | BG11847 | Positive regulator for glvARC operon |

Genes originating from other microorganisms, preferably from bacteria belonging to the genus *Bacillus*, which have the same functions as any of the *Bacillus subtilis* genes shown in Table 1, or have 70% or more homology with the nucleotide sequence of any of the genes shown in Table 1, preferably 80% or more homology, more preferably 90% or more, further preferably 95% or more, yet more preferably 98% or more, should be interpreted to be functionally equivalent to the genes shown in Table 1, and thus to constitute the genes which are to be deleted or knocked out according to the present invention.

The aforementioned genes participate in membrane permeation of maltose during incorporation thereof into cells; i.e., phosphoenolpyruvate-dependent sugar phosphotransferase system (PTS, J. Mol. Microbiol. Biotechnol., 4, 37, 2002). Specifically, the genes include a glvc gene encoding maltose-specific permease IICB involved in PTS; a glvR gene encoding a positive regulator for a glv operon containing the glvC gene; and genes functionally equivalent thereto. If any of the aforementioned genes is deleted or knocked out, maltose membrane permeability of cells is conceivably reduced. However, surprisingly, the present inventors have now found that use of a host microorganism in which any of the genes is deleted or knocked out through enzyme-producing culture employing a medium containing maltose as a predominant carbon source achieves a remarkable enhancement in productivity of protein as compared with the use of a conventional host microorganism.

Incidentally, a ptsH gene (BG10200) and a ptsI gene (BG10201) have also been known to participate in uptake of maltose in cells via PTS. Therefore, deletion or knocking out of any of ptsH and ptsI is predicted to effectively enhance productivity of protein. Thus, if a regulator gene glcT gene (BG12593), which is required for expression of a pts operon including the above two genes, is deleted or knocked out, productivity of protein should be enhanced.

An alternative method for achieving the present invention is inactivation, or knocking out, of a target gene by inserting thereto a DNA fragment of another origin or introducing a mutation to the transcription/translation-initiation region of the gene. Preferably, however, the target genes are physically deleted. The number of gene(s) to be deleted or knocked out is one or more, and two or more genes may be deleted. When a microorganism of the present invention is constructed, deletion or inactivation of a gene or genes other than those participated in membrane permeation of maltose is possible. In such a case, a more improved effect is expected.

In an example procedure for deleting or knocking out the genes, any of the target genes shown in Table 1 is deleted or knocked out according to a plan which has been set up in advance. Alternatively, randomized deletion of genes or mutation by way of knocking out is performed, followed by evaluation on protein productivity and gene analysis.

The target gene may be deleted or knocked out through homologous recombination. That is, a DNA fragment containing a portion of the target gene is cloned with an appropriate plasmid vector to thereby obtain a circular recombinant plasmid, and the resultant plasmid is transferred into cells of a parent microorganism. Thereafter, through homologous recombination effected in a partial region of the target gene, the target gene on the genome of the parent microorganism is cleaved, thereby completing inactivation of the target gene. Alternatively, the target gene is mutated (or knocked out) by substitution or insertion of a base, or a linear DNA fragment containing a region outside the target gene sequence but not containing the target gene may be constituted through PCR or a similar method, and the thus-engineered gene or fragment is transferred into a cell of a parent microorganism. At two sites outside the mutation within the target gene in the genome of the parent microorganism genome, or at two regions outside the target gene sequence, double crossing-over homologous recombination is caused to occur, to thereby attain substitution with a gene fragment in which the target gene on the genome is deleted or knocked out.

Particularly when the parent microorganism used to construct the microorganism of the present invention is *Bacillus subtilis*, since several reports have already described methods for deleting or knocking out the target gene (see, for example, Mol. Gen. Genet., 223, 268 1990), repetition of any of such methods may be followed, to thereby produce a host microorganism of the present invention.

Randomized gene deletion or inactivation may be performed through use of a method similar to the above-described method for inducing homologous recombination by use of a randomly cloned DNA fragment, or by way of irradiation of a parent microorganism with gamma rays or similar rays.

Next will be described in more detail a deletion method employing double crossing over by use of a DNA fragment designed for the deletion purpose, the DNA fragment being prepared through SOE-PCR (Gene, 77, 61, 1989). However, in the present invention, the method for deleting genes is not limited to only the below-described method.

The DNA fragment use for the deletion purpose is a fragment constructed such that a drug resistant marker gene is inserted between a ca. 0.2 to 3 kb upstream sequence which flanks and is upstream of the gene to be deleted, and a ca. 0.2 to 3 kb downstream sequence which flanks and is downstream of the same gene. In the first cycle of PCR, the following three fragments are prepared: the upstream and the downstream fragments, which are to be deleted, and the drug resistant marker gene. The primers to be used in this step may, for example, be those specifically designed so that an upstream 10-30 base pair sequence of a drug resistance gene is added to the lower end of the upstream fragment, and a downstream 10-30 base pair sequence of the drug resistance marker gene is added to the upper end of the downstream fragment (FIG. 1).

Next, using three PCR fragments prepared in the first cycle as templates, the second cycle of PCR is performed by use of an upper primer of the upstream fragment and a lower primer of the downstream fragment (out-side primers). This step causes annealing with the drug resistance marker gene fragment in the sequence of the above-engineered drug resistance marker gene, and through PCR amplification, there can be obtained a DNA fragment with the drug resistance marker gene inserted between the upstream fragment and the downstream fragment (FIG. 1).

When a chloramphenicol-resistant gene is employed as a drug resistance marker gene, a DNA fragment for deleting a gene can be obtained through SOE-PCR under typical conditions described in literature (see, for example, PCR Protocols. Current Methods and Applications, Edited by B. A. White, Humana Press, pp. 251 (1993), Gene, 77, 61, 1989), by use of an appropriate template DNA and a primer set such as that shown in Table 2 and a conventional enzyme kit for PCR (e.g., Pyrobest DNA Polymerase (product of Takara Shuzo)).

When the thus-obtained DNA fragment for effecting gene deletion is introduced into cells through the competent method or a similar method, intracellular genetic recombination occurs in homologous regions which are present upstream and downstream of the gene to be deleted. Thus, cells in which the target gene has been substituted by a drug resistance gene can be selectively separated through employment of a drug resistance marker (FIG. 1). Specifically, when a DNA fragment for gene deletion prepared by use of a primer set shown in Table 2 is introduced into cells, colonies which have grown on an agar culture medium containing chloramphenicol are separated, and deletion of the target gene by way of substitution by the chloramphenicol-resistant gene is confirmed through an appropriate method such as PCR employing a genome as a template.

Subsequently, when a gene encoding a target protein or polypeptide is transferred to a host mutant microorganism strain from which any of the *Bacillus subtilis* genes shown in Table 1, or one or more genes selected from among the genes corresponding thereto has been deleted or knocked out, the microorganism of the present invention can be obtained.

No particular limitation is imposed on the gene encoding the target protein or polypeptide. Examples of the protein and polypeptide include physiologically-active peptides and enzymes for industrial purposes such as detergents, foods, fibers, feeds, chemicals, medicine, and diagnostic agents. Industrial enzymes may be functionally grouped into oxidoreductases, transferases, hydrolases, lyases, isomerases, and ligases/synthetases. Preferably, hydrolases such as cellulase, α-amylase, and protease may be used. Specific examples include cellulase belonging to family 5 in the classification of hydrolase (Bioche M. J., 280, 309, 1991); in particular, cellulase derived from a microorganism, more particularly cellulase derived from the genus *Bacillus*. Other specific examples of the types of industrial enzymes include alkaline cellulase which is derived from the genus *Bacillus* and has an amino-acid SEQ ID NOs: 2 or 4, alkaline cellulase which has an amino-acid sequence in which one or more amino acid(s) has been deleted, substituted, or added, and cellulase which has an another amino-acid sequence having 70% homology with said amino-acid sequence, preferably 80% homology, more preferably 90%, further preferably 95%, particularly preferably 98% or more.

Specific examples of α-amylase include α-amylase derived from a microorganism, preferably liquefied amylase derived from the genus *Bacillus*. More specific examples include alkaline amylase which is derived from the genus *Bacillus* and has an amino-acid sequence of SEQ ID NO: 22, and amylase which has another amino-acid sequence having 70% homology with said amino-acid sequence, preferably 80% homology, more preferably 90%, further preferably 95%, particularly preferably 98% or more. The homology of the amino-acid sequence is calculated by the Lipman-Pearson method (Science, 227, 1435 (1985)). Specific examples of protease include serine protease and metalloprotease which are derived from microorganisms, particularly those belonging to the genus *Bacillus*.

Specific examples of protease include serine protease and metallo-protease which are derived from microorganisms, preferably those belonging to the genus *Bacillus*.

Preferably, a gene coding for a target protein or polypeptide has, on its upstream region thereof, one or more regulatory regions relating to transcription, translation, or secretion of the gene (specially, one or more regions selected from among a transcription initiation regulatory region including a promoter and a transcription initiation site; a translation initiation region including a ribosome-binding site and a start codon; and a secretion signal peptide region) properly ligated thereto. Preferably, it is preferred that three regions consisting of the transcription initiation regulatory region, the translation initiation regulatory region, and the secretion signal region be ligated to the target gene. Further preferably, the secretion signal peptide region is one that originates from the cellulase gene of a microorganism belonging to the genus *Bacillus*, and the transcription initiation region and the translation initiation region is a 0.6 to 1 kb region upstream of the cellulase gene. In one preferred example, a transcription initiation regulatory region, a translation initiation region, and a secretion signal peptide region of a cellulase gene derived from a microorganism belonging to the genus *Bacillus* disclosed in, for example, Japanese Patent Application Laid-Open (kokai) Nos. 2000-210081 and 190793/1990; i.e., a cellulase gene derived from KSM-S237 strain (FERM BP-7875) or KSM-64 strain (FERM BP-2886), is properly ligated to a structural gene of the target protein or polypeptide. More specifically, preferred DNA fragments to be ligated include a nucleotide sequence of base numbers 1 to 659 of SEQ ID NO: 1; a nucleotide sequence of base numbers 1 to 696 of a cellulase gene of SEQ ID NO: 3; a DNA fragment having a nucleotide sequence having 70% homology with any one of said nucleotide sequences, preferably 80% homology, more preferably 90%, further preferably 95%, particularly preferably 98% or more; or a DNA fragment having a nucleotide sequence lacking a portion of any one of said nucleotide sequences. Preferably, one of these DNA fragments is properly ligated to a structural gene of the target protein or polypeptide. As used herein, a DNA fragment having a nucleotide sequence lacking a portion of any one of the above-mentioned nucleotide sequences is intended to mean a DNA fragment which has functions relating to transcription, translation, and secretion of the gene, without having a portion of any one of the above-mentioned nucleotide sequences.

The recombinant microorganism of the present invention can be obtained by a conventional transformation technique in which a recombinant plasmid containing a DNA fragment which includes a gene encoding the target protein or polypeptide, and is ligated to a proper plasmid vector is transferred into a host microorganism cell. Alternatively, the recombinant microorganism may be obtained making use of a DNA fragment prepared by ligating the above DNA fragment to a proper region which is homologous with a certain portion of the host microorganism genome, and inserted directly into a host microorganism genome.

The target protein or polypeptide obtained by use of the recombinant microorganism of the present invention may be produced in such a manner that a corresponding cell strain is inoculated onto a culture medium containing assimilable carbon sources and nitrogen sources, and other essential components; the cell strain is cultured through a conventional microorganism culturing method; and subsequently, protein or polypeptide is collected and purified. No particular limitation is imposed on the ingredients and composition of a culture medium, and the medium preferably contains maltose or maltooligo saccharide as a carbon source so as to perform satisfactory culturing.

Through the aforementioned procedure, a host mutant microorganism strain in which any of the *Bacillus subtilis* genes shown in Table 1 or one or more genes selected from genes functionally equivalent thereto have been deleted or knocked out can be engineered. In addition, by use of such a mutant strain, a recombinant microorganism can be produced. Thus, a useful protein or polypeptide can be effectively produced through employment of the mutant strain or the recombinant microorganism.

Working example of the method for constructing a recombinant strain belonging to *Bacillus subtilis* from which the glvc gene (BG11848) or glvR gene (BG11847) of *Bacillus subtilis* has been deleted, and the method for producing cellulase and α-amylase by use of the recombinant microorganism will next be described in detail.

EXAMPLES

Example 1

A genome DNA sample, serving as a template, extracted from *Bacillus subtilis* 168 strain and two primer sets (glvc-AF and glvC-A/CmR; and glvC-B/CmF and glvC-BR) shown in Table 2 were used to prepare a 0.5 kb fragment (A) flanking the upstream side of the glvC gene on the genome and a 0.5 kb fragment (B) flanking the downstream side of the glvC gene. A recombinant plasmid pC194 (J. Bacteriol. 150 (2), 815 (1982))) serving as a template and a primer set formed of glvC-A/CmF and glvC-B/CmR shown in Table 2 were used to prepare a 0.9 kb fragment (C) containing the chloramphenicol-resistant gene. Subsequently, SOE-PCR was performed by use of the primers glvC-AF and glvC-BR shown in Table 2, and by use of the thus-prepared three fragments (A), (B), and (C) in combination as templates, a 1.9 kb DNA fragment in which the fragments (A), (B), and (C) were ligated in this sequence was prepared (see FIG. 1). By use of the thus-prepared DNA fragment, *Bacillus subtilis* 168 strain was transformed through the competent method. Colonies grown in an LB agar medium containing chloramphenicol were collected as transformants. The genome of the above-obtained transformant was extracted, and PCR performed thereon confirmed that the glvC gene had been deleted and substituted by a chloramphenicol-resistant gene.

Example 2

In a manner similar to that of Example 1, two primer sets (glvR-AF and glvR-A/CmR; and glvR-B/CmF and glvR-BR) shown in Table 2 were used to prepare a 0.6 kb fragment (A) flanking the upstream side of the glvR gene on the genome and a 0.6 kb fragment (B) flanking the downstream side of the glvR gene. A chloramphenicol-resistant gene of plasmid pC194 (J. Bacteriol. 150 (2), 815 (1982))) was inserted into the XbaI-BamHI cleavage site of plasmid pUC18, to thereby prepare a recombinant plasmid pCBB 31. The recombinant plasmid pCBB31 serving as a template and a primer set formed of glvR-A/CmF and glvR-B/CmR shown in Table 2 were used to prepare a 0.9 kb fragment (C) containing the chloramphenicol-resistant gene. Subsequently, SOE-OCR was performed by use of the primers glvR-AF and glvR-BR shown in Table 2, and by use of the thus-prepared three fragments (A), (B), and (C) in combination as templates, a 2.2 kb DNA fragment in which the fragments (A), (B), and (C) were ligated in this sequence was prepared (see FIG. 1). By use of the thus-prepared DNA fragment, *Bacillus subtilis* 168 strain was transformed through the competent method. Colonies grown in an LB agar medium containing chloramphenicol were collected as transformants. The genome of the above-obtained transformant was extracted, and PCR performed thereon confirmed that the glvR gene had been deleted and substituted by a chloramphenicol-resistant gene. In a similar manner, a transformant in which the glcT gene had been deleted and substituted by a chloramphenicol-resistant gene was isolated by use of two primer sets (glcT-AF and glcT-A/CmR; and glcT-B/CmF and glcT-BR).

Example 3

To each of the gene-deleted strains obtained in Examples 1 and 2 and to *Bacillus subtilis* 168 strain serving as a control, a recombinant plasmid pHY-S237 was introduced through the protoplast transformation method. The recombinant plasmid pHY-S237 was prepared by inserting a DNA fragment (3.1 kb) encoding an alkaline cellulase derived from *Bacillus* sp. KSM-S237 strain (SEQ ID NO: 1, Japanese Patent Application Laid-Open (kokai) No. 2000-210081) into the restriction enzyme BamHI cleavage site of a shuttle vector pHY300 PLK. Each of the thus-obtained cell strains was shake-cultured in an LB medium (5 mL) overnight at 30° C. The culture broth (0.03 mL) was inoculated to a 2×L-maltose medium (2% tryptone, 1% yeast extract, 1% NaCl, 7.5% maltose, 7.5 ppm manganese sulfate 4-5 hydrate, and 15 ppm tetracycline), followed by shake culturing at 30° C. for three days. After completion of culturing, cells were removed through centrifugation, and alkaline cellulase activity of the supernatant obtained from the culture was determined, thereby calculating the amount of the alkaline cellulase secreted from the cells during culturing; i.e., the amount of the extracellularly produced alkaline cellulase. As is clear from Table 3, more effective production, or secretion, of alkaline cellulase has been confirmed in all cases where a gene-deleted spore-form-

TABLE 2

| Primer | Nucleotide sequence | SEQ ID NO: |
|---|---|---|
| glvC-AF | AAATGCGCAAAAGATATGCGC | 5 |
| glvC-A/CmR | CTAATGGGTGCTTTAGTTGCTGATACCGACGATAATGCC | 6 |
| glvC-B/CmF | CTGCCCCGTTAGTTGAAGAGACTGCCCTCCTTTTCGG | 7 |
| glvC-BR | CGCAAACTCATAAAAATCATATTT | 8 |
| glvC-A/CmF | CAACTAAAGCACCCATTAGTTCAACA | 9 |
| glvC-B/CmR | CTTCAACTAACGGGGCAGGTTAGTGAC | 10 |
| glvR-AF | CAGATGATATGGTGAAAAAATCAAATCCG | 11 |
| glvR-A/CmR | GTTATCCGCTCACAATTCCGAGCTGCATATCAGATCCC | 12 |
| glvR-B/CmF | CGTCGTGACTGGGAAAACTGTTGATTACAAAGAGGCAG | 13 |
| glvR-BR | CCATCGGCCAAATATAAGACACAGCCAACGC | 14 |
| glvR-A/CmF | GAATTGTGAGCGGATAAC | 15 |
| glvR-B/CmR | GTTTTCCCAGTCACGACG | 16 |
| glcT-AF | ATAATGCCCGCTTCCCAACC | 17 |
| glcT-A/CmR | GTTATCCGCTCACAATTCCGATCCTCAGCTCCTTTGTC | 18 |
| glcT-B/CmF | CGTCGTGACTGGGAAAACTCATCTGATACCGATTAACC | 19 |
| glcT-BR | CAACTGAATCCGAAGGAATG | 20 | able strain was employed as a host, as compared with the control 168 strain (wild type strain).

TABLE 3

| Name of deleted gene | Gene ID | Gene size (bp) | Size of deleted fragment (bp) | Amount of produced (secreted) alkaline cellulase (relative value) |
|---|---|---|---|---|
| glvC | BG11848 | 1584 | 1498 | 161 |
| glvR | BG11847 | 715 | 765 | 140 |
| glcT | BG12593 | 858 | 811 | 110 |
| None (Wild type) | — | — | — | 100 |

Example 4

To each of the gene-deleted strains obtained in Examples 1 to 3 and to *Bacillus subtilis* 168 strain serving as a control, recombinant plasmid pHSP-K38 was introduced through the protoplast transformation method. The recombinant plasmid pHSP-K38 was prepared by inserting, into the restriction enzyme BagII-XbaI cleavage site of a shuttle vector pHY300 PLK, a 2.1 kb fragment (SEQ ID No: 21) prepared by ligating an upstream 0.6 kb fragment (SEQ ID NO: 3) including portions of a promoter region and a signal sequence region of an alkaline cellulase gene with an upstream side of a DNA fragment (1.5 kb) encoding a mature enzyme region (Asp1-Gln480) of an alkaline amylase gene derived from *Bacillus* sp. KSM-K38 strain (Japanese Patent Application Laid-Open (kokai) No. 2000-184882, Eur. J. Biochem., 268, 2974 (2001)). Each of the thus-obtained cell strains was shake-cultured in an LB medium (5 mL) overnight at 30° C. The culture broth (0.03 mL) was inoculated to a 2×L-maltose medium (2% tryptone, 1% yeast extract, 1% NaCl, 7.5% maltose, 7.5 ppm manganese sulfate 4-5 hydrate, and 15 ppm tetracycline), followed by shake culturing at 30° C. for three to six days. After completion of culturing, cells were removed through centrifugation, and alkaline amylase activity of the supernatant obtained from the culture was determined, thereby calculating the amount of the alkaline amylase secreted from the cells during culturing; i.e., the amount of the extracellularly produced alkaline amylase. As is clear from Table 4, more effective production, or secretion, of alkaline amylase has been confirmed in the case where a gene-deleted strain was employed as a host, as compared with the control 168 strain (wild type strain).

TABLE 4

| Name of deleted gene | Gene ID | Gene size (bp) | Size of deleted fragment (bp) | Amount of produced (secreted) alkaline amylase (relative value) |
|---|---|---|---|---|
| glvC | BG11848 | 1584 | 1498 | 202 |
| glvR | BG11847 | 715 | 765 | 153 |
| None (Wild type) | — | — | — | 100 |

The invention claimed is:

1. A recombinant microorganism prepared by transferring, to a mutant strain of microorganism from which at least one gene participating in membrane permeation of maltose has been deleted or knocked out, a gene encoding a heterologous protein selected from the group consisting of an oxidoreductase, an isomerase, an α-amylase, and a protease.

2. The recombinant microorganism as claimed in claim 1, wherein the gene participating in membrane permeation of maltose is a *Bacillus subtilis* gene glvR or glvC.

3. The recombinant microorganism as claimed in claim 1, wherein the microorganism is a member of the genus *Bacillus*.

4. The recombinant microorganism as claimed in claim 1, wherein one or more regions selected from among a transcription initiation regulatory region, a translation initiation regulatory region, and a secretion signal region is ligated to an upstream region of said gene encoding a heterologous protein.

5. The recombinant microorganism as claimed in claim 4, wherein the one or more regions are three regions constituted by a transcription initiation regulatory region, a translation initiation regulatory region, and a secretion signal region.

6. The recombinant microorganism as claimed in claim 5, wherein the secretion signal region is derived from a cellulase gene of a bacterium belonging to the genus *Bacillus* and the transcription initiation regulatory region and the translation initiation regulatory region are each derived from a 0.6 to 1 kb region upstream of the cellulase gene.

7. The recombinant microorganism as claimed in claim 5, wherein the three regions constituted by the transcription initiation regulatory region, the translation initiation regulatory region, and the secretion signal region are a nucleotide sequence of base numbers 1 to 659 of a cellulase gene of SEQ ID NO: 1; a nucleotide sequence of base numbers 1 to 696 of a cellulase gene of SEQ ID NO: 3; a DNA fragment having a nucleotide sequence having 70% identity with either of these nucleotide sequences.

8. The recombinant microorganism as claimed in claim 1, wherein the gene participating in membrane permeation of maltose encodes a PTS maltose-specific enzyme IICB.

9. The recombinant microorganism as claimed in claim 1, wherein the gene participating in membrane permeation of maltose encodes a positive regulator for the glvARC operon.

10. The recombinant microorganism as claimed in claim 1, wherein the microorganism is *Bacillus subtilis*.

11. The recombinant microorganism as claimed in claim 1, wherein said heterologous protein is an oxidoreductase.

12. The recombinant microorganism as claimed in claim 1, wherein said heterologous protein is an isomerase.

13. The recombinant microorganism as claimed in claim 1, wherein said heterologous protein is an α-amylase.

14. The recombinant microorganism as claimed in claim 1, wherein said heterologous protein is a protease.

15. A method for producing a protein by employment of a recombinant microorganism as defined in claim 1, comprising culturing said microorganism, collecting said protein in said microorganism, and purifying said protein.

16. A method for producing a protein, comprising culturing a recombinant microorganism as defined in claim 1 in a culture medium containing maltose, collecting said protein in said microorganism, and purifying said protein.

17. A recombinant microorganism prepared by transferring, to a mutant strain of microorganism from which at least one gene participating in membrane permeation of maltose has been deleted or knocked out, a gene encoding a heterologous protein selected from the group consisting of an oxidoreductase, an isomerase, an α-amylase, and a protease,
wherein three regions constituted by a transcription initiation regulatory region, a translation initiation regulatory region, and a secretion signal region are ligated to an upstream region of the gene encoding the heterologous protein,
wherein the secretion signal region is derived from a cellulase gene of a bacterium belonging to the genus *Bacillus* and the transcription initiation regulatory region and the translation initiation regulatory region are each derived from a 0.6 to 1 kb region upstream of the cellulase gene.

18. The recombinant microorganism as claimed in claim 17, wherein the gene participating in membrane permeation of maltose encodes a PTS maltose-specific enzyme IICB.

19. The recombinant microorganism as claimed in claim 17, wherein the gene participating in membrane permeation of maltose encodes a positive regulator for the glvARC operon.

20. The recombinant microorganism as claimed in claim 17, wherein the microorganism is *Bacillus subtilis*.

21. The recombinant microorganism as claimed in claim 17, wherein said heterologous protein is an oxidoreductase.

22. The recombinant microorganism as claimed in claim 17, wherein said heterologous protein is an isomerase.

23. The recombinant microorganism as claimed in claim 17, wherein said heterologous protein is an α-amylase.

24. The recombinant microorganism as claimed in claim 17, wherein said heterologous protein is a protease.

25. A method for producing a protein by employment of a recombinant microorganism as defined in claim 17, comprising culturing said microorganism, collecting said protein in said microorganism, and purifying said protein.

26. A method for producing a protein, comprising culturing a recombinant microorganism as defined in claim 17 in a culture medium containing maltose, collecting said protein in said microorganism, and purifying said protein.

27. A recombinant microorganism prepared by transferring, to a mutant strain of microorganism from which at least one gene participating in membrane permeation of maltose has been deleted or knocked out, a gene encoding a heterologous protein selected from the group consisting of an oxidoreductase, an isomerase, an α-amylase, and a protease,
wherein three regions constituted by a transcription initiation regulatory region, a translation initiation regulatory region, and a secretion signal region are ligated to an upstream region of the gene encoding the heterologous protein,
wherein the three regions constituted by the transcription initiation regulatory region, the translation initiation regulatory region, and the secretion signal region are a nucleotide sequence of base numbers 1 to 659 of a cellulase gene of SEQ ID NO: 1; a nucleotide sequence of base numbers 1 to 696 of a cellulase gene of SEQ ID NO: 3; a DNA fragment having a nucleotide sequence having 70% identity with either of these nucleotide sequences.

28. The recombinant microorganism as claimed in claim 27, wherein the gene participating in membrane permeation of maltose encodes a PTS maltose-specific enzyme IICB.

29. The recombinant microorganism as claimed in claim 27, wherein the gene participating in membrane permeation of maltose encodes a positive regulator for the glvARC operon.

30. The recombinant microorganism as claimed in claim 27, wherein the microorganism is *Bacillus subtilis*.

31. The recombinant microorganism as claimed in claim 27, wherein said heterologous protein is an oxidoreductase.

32. The recombinant microorganism as claimed in claim 27, wherein said heterologous protein is an isomerase.

33. The recombinant microorganism as claimed in claim 27, wherein said heterologous protein is an α-amylase.

34. The recombinant microorganism as claimed in claim 27, wherein said heterologous protein is a protease.

35. A method for producing a protein or polypeptide by employment of a recombinant microorganism as defined in claim 27, comprising culturing said microorganism, collecting said protein in said microorganism, and purifying said protein.

36. A method for producing a protein or polypeptide, comprising culturing a recombinant microorganism as defined in claim 27 in a culture medium containing maltose, collecting said protein in said microorganism, and purifying said protein.

* * * * *

SEQUENCE LISTING

```
<160> NUMBER OF SEQ ID NOS: 22

<210> SEQ ID NO 1
<211> LENGTH: 3150
<212> TYPE: DNA
<213> ORGANISM: Bacillus sp. KSM-S237
<220> FEATURE:
<221> NAME/KEY: CDS
<222> LOCATION: (573)..(3044)
<220> FEATURE:
<221> NAME/KEY: sig_peptide
<222> LOCATION: (573)..(659)

<400> SEQUENCE: 1
gatttgccga tgcaacaggc ttatatttag aggaaatttc tttttaaatt gaatacggaa      60
taaaatcagg taaacaggtc ctgattttat tttttttgagt tttttagaga actgaagatt    120
gaaataaaag tagaagacaa aggacataag aaaattgcat tagtttttaat tatagaaaac   180 gccttttttat aattatttat acctagaacg aaaatactgt ttcgaaagcg gtttactata    240
aaaccttata ttccggctct tttttaaaac aggggggtaaa aattcactct agtattctaa   300
tttcaacatg ctataataaa tttgtaagac gcaatatgca tctctttttt tacgatatat    360
gtaagcggtt aaccttgtgc tatatgccga tttaggaagg ggggtagatt gagtcaagta    420
gtaataatat agataactta taagttgttg agaagcagga gagcatctgg gttactcaca    480 agtttttttta aaactttaac gaaagcactt tcggtaatgc ttatgaattt agctattttga    540 ttcaattact ttaaaaatat ttaggaggta at atg atg tta aga aag aaa aca       593
                                   Met Met Leu Arg Lys Lys Thr
                                   1               5
```

-continued

| | | |
|---|---|---|
| aag cag ttg att tct tcc att ctt att tta gtt tta ctt cta tct tta<br>Lys Gln Leu Ile Ser Ser Ile Leu Ile Leu Val Leu Leu Leu Ser Leu<br>10              15                      20 | 641 | |
| ttt ccg gca gct ctt gca gca gaa gga aac act cgt gaa gac aat ttt<br>Phe Pro Ala Ala Leu Ala Ala Glu Gly Asn Thr Arg Glu Asp Asn Phe<br>25                  30                      35 | 689 | |
| aaa cat tta tta ggt aat gac aat gtt aaa cgc cct tct gag gct ggc<br>Lys His Leu Leu Gly Asn Asp Asn Val Lys Arg Pro Ser Glu Ala Gly<br>40                  45                  50                  55 | 737 | |
| gca tta caa tta caa gaa gtc gat gga caa atg aca tta gta gat caa<br>Ala Leu Gln Leu Gln Glu Val Asp Gly Gln Met Thr Leu Val Asp Gln<br>60                  65                  70 | 785 | |
| cat gga gaa aaa att caa tta cgt gga atg agt aca cac gga tta cag<br>His Gly Glu Lys Ile Gln Leu Arg Gly Met Ser Thr His Gly Leu Gln<br>75                  80                      85 | 833 | |
| tgg ttt cct gag atc ttg aat gat aac gca tac aaa gct ctt tct aac<br>Trp Phe Pro Glu Ile Leu Asn Asp Asn Ala Tyr Lys Ala Leu Ser Asn<br>90                  95                      100 | 881 | |
| gat tgg gat tcc aat atg att cgt ctt gct atg tat gta ggt gaa aat<br>Asp Trp Asp Ser Asn Met Ile Arg Leu Ala Met Tyr Val Gly Glu Asn<br>105                  110                      115 | 929 | |
| ggg tac gct aca aac cct gag tta atc aaa caa aga gtg att gat gga<br>Gly Tyr Ala Thr Asn Pro Glu Leu Ile Lys Gln Arg Val Ile Asp Gly<br>120                  125                  130                  135 | 977 | |
| att gag tta gcg att gaa aat gac atg tat gtt att gtt gac tgg cat<br>Ile Glu Leu Ala Ile Glu Asn Asp Met Tyr Val Ile Val Asp Trp His<br>140                  145                      150 | 1025 | |
| gtt cat gcg cca ggt gat cct aga gat cct gtt tat gca ggt gct aaa<br>Val His Ala Pro Gly Asp Pro Arg Asp Pro Val Tyr Ala Gly Ala Lys<br>155                  160                      165 | 1073 | |
| gat ttc ttt aga gaa att gca gct tta tac cct aat aat cca cac att<br>Asp Phe Phe Arg Glu Ile Ala Ala Leu Tyr Pro Asn Asn Pro His Ile<br>170                  175                      180 | 1121 | |
| att tat gag tta gcg aat gag ccg agt agt aat aat aat ggt gga gca<br>Ile Tyr Glu Leu Ala Asn Glu Pro Ser Ser Asn Asn Asn Gly Gly Ala<br>185                  190                      195 | 1169 | |
| ggg att ccg aat aac gaa gaa ggt tgg aaa gcg gta aaa gaa tat gct<br>Gly Ile Pro Asn Asn Glu Glu Gly Trp Lys Ala Val Lys Glu Tyr Ala<br>200                  205                  210                  215 | 1217 | |
| gat cca att gta gaa atg tta cgt aaa agc ggt aat gca gat gac aac<br>Asp Pro Ile Val Glu Met Leu Arg Lys Ser Gly Asn Ala Asp Asp Asn<br>220                  225                      230 | 1265 | |
| att atc att gtt ggt agt cca aac tgg agt cag cgt ccg gac tta gca<br>Ile Ile Ile Val Gly Ser Pro Asn Trp Ser Gln Arg Pro Asp Leu Ala<br>235                  240                      245 | 1313 | |
| gct gat aat cca att gat gat cac cat aca atg tat act gtt cac ttc<br>Ala Asp Asn Pro Ile Asp Asp His His Thr Met Tyr Thr Val His Phe<br>250                  255                      260 | 1361 | |
| tac act ggt tca cat gct gct tca act gaa agc tat ccg tct gaa act<br>Tyr Thr Gly Ser His Ala Ala Ser Thr Glu Ser Tyr Pro Ser Glu Thr<br>265                  270                      275 | 1409 | |
| cct aac tct gaa aga gga aac gta atg agt aac act cgt tat gcg tta<br>Pro Asn Ser Glu Arg Gly Asn Val Met Ser Asn Thr Arg Tyr Ala Leu<br>280                  285                  290                  295 | 1457 | |
| gaa aac gga gta gcg gta ttt gca aca gag tgg gga acg agt caa gct<br>Glu Asn Gly Val Ala Val Phe Ala Thr Glu Trp Gly Thr Ser Gln Ala<br>300                  305                      310 | 1505 | |
| agt gga gac ggt ggt cct tac ttt gat gaa gca gat gta tgg att gaa<br>Ser Gly Asp Gly Gly Pro Tyr Phe Asp Glu Ala Asp Val Trp Ile Glu<br>315                  320                      325 | 1553 | |

-continued

| | |
|---|---|
| ttt tta aat gaa aac aac att agc tgg gct aac tgg tct tta acg aat<br>Phe Leu Asn Glu Asn Asn Ile Ser Trp Ala Asn Trp Ser Leu Thr Asn<br>330                    335                    340 | 1601 |
| aaa aat gaa gta tct ggt gca ttt aca cca ttc gag tta ggt aag tct<br>Lys Asn Glu Val Ser Gly Ala Phe Thr Pro Phe Glu Leu Gly Lys Ser<br>345                    350                    355 | 1649 |
| aac gca acc aat ctt gac cca ggt cca gat cat gtg tgg gca cca gaa<br>Asn Ala Thr Asn Leu Asp Pro Gly Pro Asp His Val Trp Ala Pro Glu<br>360                    365                    370                    375 | 1697 |
| gaa tta agt ctt tct gga gaa tat gta cgt gct cgt att aaa ggt gtg<br>Glu Leu Ser Leu Ser Gly Glu Tyr Val Arg Ala Arg Ile Lys Gly Val<br>380                    385                    390 | 1745 |
| aac tat gag cca atc gac cgt aca aaa tac acg aaa gta ctt tgg gac<br>Asn Tyr Glu Pro Ile Asp Arg Thr Lys Tyr Thr Lys Val Leu Trp Asp<br>395                    400                    405 | 1793 |
| ttt aat gat gga acg aag caa gga ttt gga gtg aat tcg gat tct cca<br>Phe Asn Asp Gly Thr Lys Gln Gly Phe Gly Val Asn Ser Asp Ser Pro<br>410                    415                    420 | 1841 |
| aat aaa gaa ctt att gca gtt gat aat gaa aac aac act ttg aaa gtt<br>Asn Lys Glu Leu Ile Ala Val Asp Asn Glu Asn Asn Thr Leu Lys Val<br>425                    430                    435 | 1889 |
| tcg gga tta gat gta agt aac gat gtt tca gat ggc aac ttc tgg gct<br>Ser Gly Leu Asp Val Ser Asn Asp Val Ser Asp Gly Asn Phe Trp Ala<br>440                    445                    450                    455 | 1937 |
| aat gct cgt ctt tct gcc aac ggt tgg gga aaa agt gtt gat att tta<br>Asn Ala Arg Leu Ser Ala Asn Gly Trp Gly Lys Ser Val Asp Ile Leu<br>460                    465                    470 | 1985 |
| ggt gct gag aag ctt aca atg gat gtt att gtt gat gaa cca acg acg<br>Gly Ala Glu Lys Leu Thr Met Asp Val Ile Val Asp Glu Pro Thr Thr<br>475                    480                    485 | 2033 |
| gta gct att gcg gcg att cca caa agt agt aaa agt gga tgg gca aat<br>Val Ala Ile Ala Ala Ile Pro Gln Ser Ser Lys Ser Gly Trp Ala Asn<br>490                    495                    500 | 2081 |
| cca gag cgt gct gtt cga gtg aac gcg gaa gat ttt gtc cag caa acg<br>Pro Glu Arg Ala Val Arg Val Asn Ala Glu Asp Phe Val Gln Gln Thr<br>505                    510                    515 | 2129 |
| gac ggt aag tat aaa gct gga tta aca att aca gga gaa gat gct cct<br>Asp Gly Lys Tyr Lys Ala Gly Leu Thr Ile Thr Gly Glu Asp Ala Pro<br>520                    525                    530                    535 | 2177 |
| aac cta aaa aat atc gct ttt cat gaa gaa gat aac aat atg aac aac<br>Asn Leu Lys Asn Ile Ala Phe His Glu Glu Asp Asn Asn Met Asn Asn<br>540                    545                    550 | 2225 |
| atc att ctg ttc gtg gga act gat gca gct gac gtt att tac tta gat<br>Ile Ile Leu Phe Val Gly Thr Asp Ala Ala Asp Val Ile Tyr Leu Asp<br>555                    560                    565 | 2273 |
| aac att aaa gta att gga aca gaa gtt gaa att cca gtt gtt cat gat<br>Asn Ile Lys Val Ile Gly Thr Glu Val Glu Ile Pro Val Val His Asp<br>570                    575                    580 | 2321 |
| cca aaa gga gaa gct gtt ctt cct tct gtt ttt gaa gac ggt aca cgt<br>Pro Lys Gly Glu Ala Val Leu Pro Ser Val Phe Glu Asp Gly Thr Arg<br>585                    590                    595 | 2369 |
| caa ggt tgg gac tgg gct gga gag tct ggt gtg aaa aca gct tta aca<br>Gln Gly Trp Asp Trp Ala Gly Glu Ser Gly Val Lys Thr Ala Leu Thr<br>600                    605                    610                    615 | 2417 |
| att gaa gaa gca aac ggt tct aac gcg tta tca tgg gaa ttt gga tat<br>Ile Glu Glu Ala Asn Gly Ser Asn Ala Leu Ser Trp Glu Phe Gly Tyr<br>620                    625                    630 | 2465 |
| cca gaa gta aaa cct agt gat aac tgg gca aca gct cca cgt tta gat<br>Pro Glu Val Lys Pro Ser Asp Asn Trp Ala Thr Ala Pro Arg Leu Asp | 2513 |

```
                      635                 640                 645
ttc tgg aaa tct gac ttg gtt cgc ggt gag aat gat tat gta gct ttt      2561
Phe Trp Lys Ser Asp Leu Val Arg Gly Glu Asn Asp Tyr Val Ala Phe
650                 655                 660 gat ttc tat cta gat cca gtt cgt gca aca gaa ggc gca atg aat atc      2609
Asp Phe Tyr Leu Asp Pro Val Arg Ala Thr Glu Gly Ala Met Asn Ile
665                 670                 675 aat tta gta ttc cag cca cct act aac ggg tat tgg gta caa gca cca      2657
Asn Leu Val Phe Gln Pro Pro Thr Asn Gly Tyr Trp Val Gln Ala Pro
680                 685                 690                 695 aaa acg tat acg att aac ttt gat gaa tta gag gaa gcg aat caa gta      2705
Lys Thr Tyr Thr Ile Asn Phe Asp Glu Leu Glu Glu Ala Asn Gln Val
700                 705                 710 aat ggt tta tat cac tat gaa gtg aaa att aac gta aga gat att aca      2753
Asn Gly Leu Tyr His Tyr Glu Val Lys Ile Asn Val Arg Asp Ile Thr
715                 720                 725 aac att caa gat gac acg tta cta cgt aac atg atg atc att ttt gca      2801
Asn Ile Gln Asp Asp Thr Leu Leu Arg Asn Met Met Ile Ile Phe Ala
730                 735                 740 gat gta gaa agt gac ttt gca ggg aga gtc ttt gta gat aat gtt cgt      2849
Asp Val Glu Ser Asp Phe Ala Gly Arg Val Phe Val Asp Asn Val Arg
745                 750                 755 ttt gag ggg gct gct act act gag ccg gtt gaa cca gag cca gtt gat      2897
Phe Glu Gly Ala Ala Thr Thr Glu Pro Val Glu Pro Glu Pro Val Asp
760                 765                 770                 775 cct ggc gaa gag acg cca cct gtc gat gag aag gaa gcg aaa aaa gaa      2945
Pro Gly Glu Glu Thr Pro Pro Val Asp Glu Lys Glu Ala Lys Lys Glu
780                 785                 790 caa aaa gaa gca gag aaa gaa gag aaa gaa gca gta aaa gaa gaa aag      2993
Gln Lys Glu Ala Glu Lys Glu Glu Lys Glu Ala Val Lys Glu Glu Lys
795                 800                 805 aaa gaa gct aaa gaa gaa aag aaa gca gtc aaa aat gag gct aag aaa      3041
Lys Glu Ala Lys Glu Glu Lys Lys Ala Val Lys Asn Glu Ala Lys Lys
810                 815                 820 aaa taatctatta aactagttat agggttatct aaaggtctga tgtagatctt           3094
Lys
ttagataacc ttttcttgc ataactggac acagagttgt tattaaagaa agtaag         3150

<210> SEQ ID NO 2
<211> LENGTH: 824
<212> TYPE: PRT
<213> ORGANISM: Bacillus sp. KSM-S237

<400> SEQUENCE: 2

Met Met Leu Arg Lys Lys Thr Lys Gln Leu Ile Ser Ser Ile Leu Ile
1               5                   10                  15

Leu Val Leu Leu Leu Ser Leu Phe Pro Ala Ala Leu Ala Ala Glu Gly
20                  25                  30

Asn Thr Arg Glu Asp Asn Phe Lys His Leu Leu Gly Asn Asp Asn Val
35                  40                  45

Lys Arg Pro Ser Glu Ala Gly Ala Leu Gln Leu Gln Glu Val Asp Gly
50                  55                  60

Gln Met Thr Leu Val Asp Gln His Gly Glu Lys Ile Gln Leu Arg Gly
65              70                  75                  80

Met Ser Thr His Gly Leu Gln Trp Phe Pro Glu Ile Leu Asn Asp Asn
85                  90                  95

Ala Tyr Lys Ala Leu Ser Asn Asp Trp Asp Ser Asn Met Ile Arg Leu
100                 105                 110
```

```
Ala Met Tyr Val Gly Glu Asn Gly Tyr Ala Thr Asn Pro Glu Leu Ile
115                 120                 125

Lys Gln Arg Val Ile Asp Gly Ile Glu Leu Ala Ile Glu Asn Asp Met
130                 135                 140

Tyr Val Ile Val Asp Trp His Val His Ala Pro Gly Asp Pro Arg Asp
145                 150                 155                 160

Pro Val Tyr Ala Gly Ala Lys Asp Phe Phe Arg Glu Ile Ala Ala Leu
165                 170                 175

Tyr Pro Asn Asn Pro His Ile Ile Tyr Glu Leu Ala Asn Glu Pro Ser
180                 185                 190

Ser Asn Asn Asn Gly Gly Ala Gly Ile Pro Asn Asn Glu Glu Gly Trp
195                 200                 205

Lys Ala Val Lys Glu Tyr Ala Asp Pro Ile Val Glu Met Leu Arg Lys
210                 215                 220

Ser Gly Asn Ala Asp Asp Asn Ile Ile Ile Val Gly Ser Pro Asn Trp
225                 230                 235                 240

Ser Gln Arg Pro Asp Leu Ala Ala Asp Asn Pro Ile Asp Asp His His
245                 250                 255

Thr Met Tyr Thr Val His Phe Tyr Thr Gly Ser His Ala Ala Ser Thr
260                 265                 270

Glu Ser Tyr Pro Ser Glu Thr Pro Asn Ser Glu Arg Gly Asn Val Met
275                 280                 285

Ser Asn Thr Arg Tyr Ala Leu Glu Asn Gly Val Ala Val Phe Ala Thr
290                 295                 300

Glu Trp Gly Thr Ser Gln Ala Ser Gly Asp Gly Pro Tyr Phe Asp
305                 310                 315                 320

Glu Ala Asp Val Trp Ile Glu Phe Leu Asn Glu Asn Asn Ile Ser Trp
325                 330                 335

Ala Asn Trp Ser Leu Thr Asn Lys Asn Glu Val Ser Gly Ala Phe Thr
340                 345                 350

Pro Phe Glu Leu Gly Lys Ser Asn Ala Thr Asn Leu Asp Pro Gly Pro
355                 360                 365

Asp His Val Trp Ala Pro Glu Glu Leu Ser Leu Ser Gly Glu Tyr Val
370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
405                 410                 415

Gly Val Asn Ser Asp Ser Pro Asn Lys Glu Leu Ile Ala Val Asp Asn
420                 425                 430

Glu Asn Asn Thr Leu Lys Val Ser Gly Leu Asp Val Ser Asn Asp Val
435                 440                 445

Ser Asp Gly Asn Phe Trp Ala Asn Ala Arg Leu Ser Ala Asn Gly Trp
450                 455                 460

Gly Lys Ser Val Asp Ile Leu Gly Ala Glu Lys Leu Thr Met Asp Val
465                 470                 475                 480

Ile Val Asp Glu Pro Thr Thr Val Ala Ile Ala Ile Pro Gln Ser
485                 490                 495

Ser Lys Ser Gly Trp Ala Asn Pro Glu Arg Ala Val Arg Val Asn Ala
500                 505                 510

Glu Asp Phe Val Gln Gln Thr Asp Gly Lys Tyr Lys Ala Gly Leu Thr
515                 520                 525

Ile Thr Gly Glu Asp Ala Pro Asn Leu Lys Asn Ile Ala Phe His Glu
```

```
              530             535             540
Glu Asp Asn Asn Met Asn Asn Ile Ile Leu Phe Val Gly Thr Asp Ala
545                 550                 555                 560

Ala Asp Val Ile Tyr Leu Asp Asn Ile Lys Val Ile Gly Thr Glu Val
565                 570                 575

Glu Ile Pro Val Val His Asp Pro Lys Gly Glu Ala Val Leu Pro Ser
580                 585                 590

Val Phe Glu Asp Gly Thr Arg Gln Gly Trp Asp Trp Ala Gly Glu Ser
595                 600                 605

Gly Val Lys Thr Ala Leu Thr Ile Glu Glu Ala Asn Gly Ser Asn Ala
610                 615                 620

Leu Ser Trp Glu Phe Gly Tyr Pro Glu Val Lys Pro Ser Asp Asn Trp
625                 630                 635                 640

Ala Thr Ala Pro Arg Leu Asp Phe Trp Lys Ser Asp Leu Val Arg Gly
645                 650                 655

Glu Asn Asp Tyr Val Ala Phe Asp Phe Tyr Leu Asp Pro Val Arg Ala
660                 665                 670

Thr Glu Gly Ala Met Asn Ile Asn Leu Val Phe Gln Pro Pro Thr Asn
675                 680                 685

Gly Tyr Trp Val Gln Ala Pro Lys Thr Tyr Thr Ile Asn Phe Asp Glu
690                 695                 700

Leu Glu Glu Ala Asn Gln Val Asn Gly Leu Tyr His Tyr Glu Val Lys
705                 710                 715                 720

Ile Asn Val Arg Asp Ile Thr Asn Ile Gln Asp Asp Thr Leu Leu Arg
725                 730                 735

Asn Met Met Ile Ile Phe Ala Asp Val Glu Ser Asp Phe Ala Gly Arg
740                 745                 750

Val Phe Val Asp Asn Val Arg Phe Glu Gly Ala Ala Thr Thr Glu Pro
755                 760                 765

Val Glu Pro Glu Pro Val Asp Pro Gly Glu Glu Thr Pro Pro Val Asp
770                 775                 780

Glu Lys Glu Ala Lys Lys Glu Gln Lys Glu Ala Glu Lys Glu Glu Lys
785                 790                 795                 800

Glu Ala Val Lys Glu Glu Lys Lys Glu Ala Lys Glu Glu Lys Lys Ala
805                 810                 815

Val Lys Asn Glu Ala Lys Lys Lys
820

<210> SEQ ID NO 3
<211> LENGTH: 3332
<212> TYPE: DNA
<213> ORGANISM: Bacillus sp. KSM-64
<220> FEATURE:
<221> NAME/KEY: CDS
<222> LOCATION: (610)..(3075)
<220> FEATURE:
<221> NAME/KEY: sig_peptide
<222> LOCATION: (610)..(696)

<400> SEQUENCE: 3
agtacttacc attttagagt caaaagatag aagccaagca ggatttgccg atgcaaccgg      60
cttatattta gagggaattt cttttttaaat tgaatacgga ataaaatcag gtaaacaggt    120
cctgatttta ttttttttgaa ttttttttgag aactaaagat tgaaatagaa gtagaagaca   180
acggacataa gaaaattgta ttagttttaa ttatagaaaa cgcttttcta taattattta    240
tacctagaac gaaaatactg tttcgaaagc ggtttactat aaaaccttat attccggctc    300
```

```
                                              -continued ttttttttaaa caggggggtga aaattcactc tagtattcta atttcaacat gctataataa    360
atttgtaaga cgcaatatac atcttttttt tatgatattt gtaagcggtt aaccttgtgc    420
tatatgccga tttaggaagg gggtagattg agtcaagtag tcataattta gataacttat    480
aagttgttga gaagcaggag agaatctggg ttactcacaa gttttttaaa acattatcga    540
aagcactttc ggttatgctt atgaatttag ctatttgatt caattacttt aataatttta    600 ggaggtaat atg atg tta aga aag aaa aca aag cag ttg att tct tcc att    651
          Met Met Leu Arg Lys Lys Thr Lys Gln Leu Ile Ser Ser Ile
          1               5                  10 ctt att tta gtt tta ctt cta tct tta ttt ccg aca gct ctt gca gca    699
Leu Ile Leu Val Leu Leu Leu Ser Leu Phe Pro Thr Ala Leu Ala Ala
15              20                  25                  30 gaa gga aac act cgt gaa gac aat ttt aaa cat tta tta ggt aat gac    747
Glu Gly Asn Thr Arg Glu Asp Asn Phe Lys His Leu Leu Gly Asn Asp
            35                  40                  45 aat gtt aaa cgc cct tct gag gct ggc gca tta caa tta caa gaa gtc    795
Asn Val Lys Arg Pro Ser Glu Ala Gly Ala Leu Gln Leu Gln Glu Val
50              55                  60 gat gga caa atg aca tta gta gat caa cat gga gaa aaa att caa tta    843
Asp Gly Gln Met Thr Leu Val Asp Gln His Gly Glu Lys Ile Gln Leu
65              70                  75 cgt gga atg agt aca cac gga tta caa tgg ttt cct gag atc ttg aat    891
Arg Gly Met Ser Thr His Gly Leu Gln Trp Phe Pro Glu Ile Leu Asn
80              85                  90 gat aac gca tac aaa gct ctt gct aac gat tgg gaa tca aat atg att    939
Asp Asn Ala Tyr Lys Ala Leu Ala Asn Asp Trp Glu Ser Asn Met Ile
95              100                 105                 110 cgt cta gct atg tat gtc ggt gaa aat ggc tat gct tca aat cca gag    987
Arg Leu Ala Met Tyr Val Gly Glu Asn Gly Tyr Ala Ser Asn Pro Glu
115             120                 125 tta att aaa agc aga gtc att aaa gga ata gat ctt gct att gaa aat   1035
Leu Ile Lys Ser Arg Val Ile Lys Gly Ile Asp Leu Ala Ile Glu Asn
130             135                 140 gac atg tat gtc atc gtt gat tgg cat gta cat gca cct ggt gat cct   1083
Asp Met Tyr Val Ile Val Asp Trp His Val His Ala Pro Gly Asp Pro
145             150                 155 aga gat ccc gtt tac gct gga gca gaa gat ttc ttt aga gat att gca   1131
Arg Asp Pro Val Tyr Ala Gly Ala Glu Asp Phe Phe Arg Asp Ile Ala
160             165                 170 gca tta tat cct aac aat cca cac att att tat gag tta gcg aat gag   1179
Ala Leu Tyr Pro Asn Asn Pro His Ile Ile Tyr Glu Leu Ala Asn Glu
175             180                 185                 190 cca agt agt aac aat aat ggt gga gct ggg att cca aat aat gaa gaa   1227
Pro Ser Ser Asn Asn Asn Gly Gly Ala Gly Ile Pro Asn Asn Glu Glu
195             200                 205 ggt tgg aat gcg gta aaa gaa tac gct gat cca att gta gaa atg tta   1275
Gly Trp Asn Ala Val Lys Glu Tyr Ala Asp Pro Ile Val Glu Met Leu
210             215                 220 cgt gat agc ggg aac gca gat gac aat att atc att gtg ggt agt cca   1323
Arg Asp Ser Gly Asn Ala Asp Asp Asn Ile Ile Ile Val Gly Ser Pro
225             230                 235 aac tgg agt cag cgt cct gac tta gca gct gat aat cca att gat gat   1371
Asn Trp Ser Gln Arg Pro Asp Leu Ala Ala Asp Asn Pro Ile Asp Asp
240             245                 250 cac cat aca atg tat act gtt cac ttc tac act ggt tca cat gct gct   1419
His His Thr Met Tyr Thr Val His Phe Tyr Thr Gly Ser His Ala Ala
255             260                 265                 270
```

```
tca act gaa agc tat ccg cct gaa act cct aac tct gaa aga gga aac     1467
Ser Thr Glu Ser Tyr Pro Pro Glu Thr Pro Asn Ser Glu Arg Gly Asn
275                 280                 285 gta atg agt aac act cgt tat gcg tta gaa aac gga gta gca gta ttt     1515
Val Met Ser Asn Thr Arg Tyr Ala Leu Glu Asn Gly Val Ala Val Phe
        290                 295                 300 gca aca gag tgg gga act agc caa gca aat gga gat ggt ggt cct tac     1563
Ala Thr Glu Trp Gly Thr Ser Gln Ala Asn Gly Asp Gly Gly Pro Tyr
305                 310                 315 ttt gat gaa gca gat gta tgg att gag ttt tta aat gaa aac aac att     1611
Phe Asp Glu Ala Asp Val Trp Ile Glu Phe Leu Asn Glu Asn Asn Ile
320                 325                 330 agc tgg gct aac tgg tct tta acg aat aaa aat gaa gta tct ggt gca     1659
Ser Trp Ala Asn Trp Ser Leu Thr Asn Lys Asn Glu Val Ser Gly Ala
335                 340                 345                 350 ttt aca cca ttc gag tta ggt aag tct aac gca aca agt ctt gac cca     1707
Phe Thr Pro Phe Glu Leu Gly Lys Ser Asn Ala Thr Ser Leu Asp Pro
        355                 360                 365 ggg cca gac caa gta tgg gta cca gaa gag tta agt ctt tct gga gaa     1755
Gly Pro Asp Gln Val Trp Val Pro Glu Glu Leu Ser Leu Ser Gly Glu
370                 375                 380 tat gta cgt gct cgt att aaa ggt gtg aac tat gag cca atc gac cgt     1803
Tyr Val Arg Ala Arg Ile Lys Gly Val Asn Tyr Glu Pro Ile Asp Arg
385                 390                 395 aca aaa tac acg aaa gta ctt tgg gac ttt aat gat gga acg aag caa     1851
Thr Lys Tyr Thr Lys Val Leu Trp Asp Phe Asn Asp Gly Thr Lys Gln
400                 405                 410 gga ttt gga gtg aat gga gat tct cca gtt gaa gat gta gtt att gag     1899
Gly Phe Gly Val Asn Gly Asp Ser Pro Val Glu Asp Val Val Ile Glu
        415                 420                 425         430 aat gaa gcg ggc gct tta aaa ctt tca gga tta gat gca agt aat gat     1947
Asn Glu Ala Gly Ala Leu Lys Leu Ser Gly Leu Asp Ala Ser Asn Asp
435                 440                 445 gtt tct gaa ggt aat tac tgg gct aat gct cgt ctt tct gcc gac ggt     1995
Val Ser Glu Gly Asn Tyr Trp Ala Asn Ala Arg Leu Ser Ala Asp Gly
450                 455                 460 tgg gga aaa agt gtt gat att tta ggt gct gaa aaa ctt act atg gat     2043
Trp Gly Lys Ser Val Asp Ile Leu Gly Ala Glu Lys Leu Thr Met Asp
465                 470                 475 gtg att gtt gat gag ccg acc acg gta tca att gct gca att cca caa     2091
Val Ile Val Asp Glu Pro Thr Thr Val Ser Ile Ala Ala Ile Pro Gln
        480                 485                 490 ggg cca tca gcc aat tgg gtt aat cca aat cgt gca att aag gtt gag     2139
Gly Pro Ser Ala Asn Trp Val Asn Pro Asn Arg Ala Ile Lys Val Glu
495                 500                 505                 510 cca act aat ttc gta ccg tta gga gat aag ttt aaa gcg gaa tta act     2187
Pro Thr Asn Phe Val Pro Leu Gly Asp Lys Phe Lys Ala Glu Leu Thr
515                 520                 525 ata act tca gct gac tct cca tcg tta gaa gct att gcg atg cat gct     2235
Ile Thr Ser Ala Asp Ser Pro Ser Leu Glu Ala Ile Ala Met His Ala
530                 535                 540 gaa aat aac aac atc aac aac atc att ctt ttt gta gga act gaa ggt     2283
Glu Asn Asn Asn Ile Asn Asn Ile Ile Leu Phe Val Gly Thr Glu Gly
545                 550                 555 gct gat gtt atc tat tta gat aac att aaa gta att gga aca gaa gtt     2331
Ala Asp Val Ile Tyr Leu Asp Asn Ile Lys Val Ile Gly Thr Glu Val
560                 565                 570 gaa att cca gtt gtt cat gat cca aaa gga gaa gct gtt ctt cct tct     2379
Glu Ile Pro Val Val His Asp Pro Lys Gly Glu Ala Val Leu Pro Ser
```

```
              575                 580                 585                 590
gtt ttt gaa gac ggt aca cgt caa ggt tgg gac tgg gct gga gag tct          2427
Val Phe Glu Asp Gly Thr Arg Gln Gly Trp Asp Trp Ala Gly Glu Ser
595                 600                 605 ggt gtg aaa aca gct tta aca att gaa gaa gca aac ggt tct aac gcg          2475
Gly Val Lys Thr Ala Leu Thr Ile Glu Glu Ala Asn Gly Ser Asn Ala
610                 615                 620 tta tca tgg gaa ttt gga tac cca gaa gta aaa cct agt gat aac tgg          2523
Leu Ser Trp Glu Phe Gly Tyr Pro Glu Val Lys Pro Ser Asp Asn Trp
625                 630                 635 gca aca gct cca cgt tta gat ttc tgg aaa tct gac ttg gtt cgc ggt          2571
Ala Thr Ala Pro Arg Leu Asp Phe Trp Lys Ser Asp Leu Val Arg Gly
640                 645                 650 gaa aat gat tat gta act ttt gat ttc tat cta gat cca gtt cgt gca          2619
Glu Asn Asp Tyr Val Thr Phe Asp Phe Tyr Leu Asp Pro Val Arg Ala
655                 660                 665                 670 aca gaa ggc gca atg aat atc aat tta gta ttc cag cca cct act aac          2667
Thr Glu Gly Ala Met Asn Ile Asn Leu Val Phe Gln Pro Pro Thr Asn
675                 680                 685 ggg tat tgg gta caa gca cca aaa acg tat acg att aac ttt gat gaa          2715
Gly Tyr Trp Val Gln Ala Pro Lys Thr Tyr Thr Ile Asn Phe Asp Glu
690                 695                 700 tta gag gaa gcg aat caa gta aat ggt tta tat cac tat gaa gtg aaa          2763
Leu Glu Glu Ala Asn Gln Val Asn Gly Leu Tyr His Tyr Glu Val Lys
705                 710                 715 att aac gta aga gat att aca aac att caa gat gac acg tta cta cgt          2811
Ile Asn Val Arg Asp Ile Thr Asn Ile Gln Asp Asp Thr Leu Leu Arg
720                 725                 730 aac atg atg atc att ttt gca gat gta gaa agt gac ttt gca ggg aga          2859
Asn Met Met Ile Ile Phe Ala Asp Val Glu Ser Asp Phe Ala Gly Arg
735                 740                 745                 750 gtc ttt gta gat aat gtt cgt ttt gag ggg gct gct act act gag ccg          2907
Val Phe Val Asp Asn Val Arg Phe Glu Gly Ala Ala Thr Thr Glu Pro
755                 760                 765 gtt gaa cca gag cca gtt gat cct ggc gaa gag acg ccg cct gtc gat          2955
Val Glu Pro Glu Pro Val Asp Pro Gly Glu Glu Thr Pro Pro Val Asp
770                 775                 780 gag aag gaa gcg aaa aaa gaa caa aaa gaa gca gag aaa gaa gag aaa          3003
Glu Lys Glu Ala Lys Lys Glu Gln Lys Glu Ala Glu Lys Glu Glu Lys
785                 790                 795 gaa gca gta aaa gaa gaa aag aaa gaa gct aaa gaa gaa aag aaa gca          3051
Glu Ala Val Lys Glu Glu Lys Lys Glu Ala Lys Glu Glu Lys Lys Ala
800                 805                 810 atc aaa aat gag gct acg aaa aaa taatctaata aactagttat agggttatct        3105
Ile Lys Asn Glu Ala Thr Lys Lys
815                 820 aaaggtctga tgcagatctt ttagataacc ttttttgca taactggaca tagaatggtt        3165
attaaagaaa gcaaggtgtt tatacgatat taaaaggta gcgattttaa attgaaacct        3225
ttaataatgt cttgtgatag aatgatgaag taatttaaga gggggaaacg aagtgaaaac      3285
ggaaatttct agtagaagaa aaacagacca agaaatactg caagctt                     3332

<210> SEQ ID NO 4
<211> LENGTH: 822
<212> TYPE: PRT
<213> ORGANISM: Bacillus sp. KSM-64

<400> SEQUENCE: 4

Met Met Leu Arg Lys Lys Thr Lys Gln Leu Ile Ser Ser Ile Leu Ile
```

-continued

```
  1               5                    10                       15
Leu Val Leu Leu Leu Ser Leu Phe Pro Thr Ala Leu Ala Ala Glu Gly
 20                  25                  30

Asn Thr Arg Glu Asp Asn Phe Lys His Leu Leu Gly Asn Asp Asn Val
 35                  40                  45

Lys Arg Pro Ser Glu Ala Gly Ala Leu Gln Leu Gln Glu Val Asp Gly
 50                  55                  60

Gln Met Thr Leu Val Asp Gln His Gly Glu Lys Ile Gln Leu Arg Gly
 65                  70                  75                  80

Met Ser Thr His Gly Leu Gln Trp Phe Pro Glu Ile Leu Asn Asp Asn
 85                  90                  95

Ala Tyr Lys Ala Leu Ala Asn Asp Trp Glu Ser Asn Met Ile Arg Leu
100                 105                 110

Ala Met Tyr Val Gly Glu Asn Gly Tyr Ala Ser Asn Pro Glu Leu Ile
115                 120                 125

Lys Ser Arg Val Ile Lys Gly Ile Asp Leu Ala Ile Glu Asn Asp Met
130                 135                 140

Tyr Val Ile Val Asp Trp His Val His Ala Pro Gly Asp Pro Arg Asp
145                 150                 155                 160

Pro Val Tyr Ala Gly Ala Glu Asp Phe Phe Arg Asp Ile Ala Ala Leu
165                 170                 175

Tyr Pro Asn Asn Pro His Ile Ile Tyr Glu Leu Ala Asn Glu Pro Ser
180                 185                 190

Ser Asn Asn Asn Gly Gly Ala Gly Ile Pro Asn Asn Glu Glu Gly Trp
195                 200                 205

Asn Ala Val Lys Glu Tyr Ala Asp Pro Ile Val Glu Met Leu Arg Asp
210                 215                 220

Ser Gly Asn Ala Asp Asp Asn Ile Ile Val Gly Ser Pro Asn Trp
225                 230                 235                 240

Ser Gln Arg Pro Asp Leu Ala Ala Asp Asn Pro Ile Asp Asp His His
245                 250                 255

Thr Met Tyr Thr Val His Phe Tyr Thr Gly Ser His Ala Ala Ser Thr
260                 265                 270

Glu Ser Tyr Pro Pro Glu Thr Pro Asn Ser Glu Arg Gly Asn Val Met
275                 280                 285

Ser Asn Thr Arg Tyr Ala Leu Glu Asn Gly Val Ala Val Phe Ala Thr
290                 295                 300

Glu Trp Gly Thr Ser Gln Ala Asn Gly Asp Gly Gly Pro Tyr Phe Asp
305                 310                 315                 320

Glu Ala Asp Val Trp Ile Glu Phe Leu Asn Glu Asn Asn Ile Ser Trp
325                 330                 335

Ala Asn Trp Ser Leu Thr Asn Lys Asn Glu Val Ser Gly Ala Phe Thr
340                 345                 350

Pro Phe Glu Leu Gly Lys Ser Asn Ala Thr Ser Leu Asp Pro Gly Pro
355                 360                 365

Asp Gln Val Trp Val Pro Glu Glu Leu Ser Leu Ser Gly Glu Tyr Val
370                 375                 380

Arg Ala Arg Ile Lys Gly Val Asn Tyr Glu Pro Ile Asp Arg Thr Lys
385                 390                 395                 400

Tyr Thr Lys Val Leu Trp Asp Phe Asn Asp Gly Thr Lys Gln Gly Phe
405                 410                 415

Gly Val Asn Gly Asp Ser Pro Val Glu Asp Val Val Ile Glu Asn Glu
420                 425                 430
```

```
Ala Gly Ala Leu Lys Leu Ser Gly Leu Asp Ala Ser Asn Asp Val Ser
435                 440                 445

Glu Gly Asn Tyr Trp Ala Asn Ala Arg Leu Ser Ala Asp Gly Trp Gly
450                 455                 460

Lys Ser Val Asp Ile Leu Gly Ala Glu Lys Leu Thr Met Asp Val Ile
465                 470                 475                 480

Val Asp Glu Pro Thr Thr Val Ser Ile Ala Ala Ile Pro Gln Gly Pro
    485                 490                 495

Ser Ala Asn Trp Val Asn Pro Asn Arg Ala Ile Lys Val Glu Pro Thr
    500                 505                 510

Asn Phe Val Pro Leu Gly Asp Lys Phe Lys Ala Glu Leu Thr Ile Thr
    515                 520                 525

Ser Ala Asp Ser Pro Ser Leu Glu Ala Ile Ala Met His Ala Glu Asn
    530                 535                 540

Asn Asn Ile Asn Asn Ile Ile Leu Phe Val Gly Thr Glu Gly Ala Asp
545                 550                 555                 560

Val Ile Tyr Leu Asp Asn Ile Lys Val Ile Gly Thr Glu Val Glu Ile
    565                 570                 575

Pro Val Val His Asp Pro Lys Gly Glu Ala Val Leu Pro Ser Val Phe
    580                 585                 590

Glu Asp Gly Thr Arg Gln Gly Trp Asp Trp Ala Gly Glu Ser Gly Val
    595                 600                 605

Lys Thr Ala Leu Thr Ile Glu Glu Ala Asn Gly Ser Asn Ala Leu Ser
610                 615                 620

Trp Glu Phe Gly Tyr Pro Glu Val Lys Pro Ser Asp Asn Trp Ala Thr
625                 630                 635                 640

Ala Pro Arg Leu Asp Phe Trp Lys Ser Asp Leu Val Arg Gly Glu Asn
    645                 650                 655

Asp Tyr Val Thr Phe Asp Phe Tyr Leu Asp Pro Val Arg Ala Thr Glu
    660                 665                 670

Gly Ala Met Asn Ile Asn Leu Val Phe Gln Pro Pro Thr Asn Gly Tyr
    675                 680                 685

Trp Val Gln Ala Pro Lys Thr Tyr Thr Ile Asn Phe Asp Glu Leu Glu
690                 695                 700

Glu Ala Asn Gln Val Asn Gly Leu Tyr His Tyr Glu Val Lys Ile Asn
705                 710                 715                 720

Val Arg Asp Ile Thr Asn Ile Gln Asp Asp Thr Leu Leu Arg Asn Met
    725                 730                 735

Met Ile Ile Phe Ala Asp Val Glu Ser Asp Phe Ala Gly Arg Val Phe
    740                 745                 750

Val Asp Asn Val Arg Phe Glu Gly Ala Ala Thr Thr Glu Pro Val Glu
    755                 760                 765

Pro Glu Pro Val Asp Pro Gly Glu Glu Thr Pro Val Asp Glu Lys
    770                 775                 780

Glu Ala Lys Lys Glu Gln Lys Glu Ala Glu Lys Glu Lys Glu Ala
    785                 790                 795                 800

Val Lys Glu Glu Lys Lys Glu Ala Lys Glu Glu Lys Lys Ala Ile Lys
805                 810                 815

Asn Glu Ala Thr Lys Lys
820

<210> SEQ ID NO 5
<211> LENGTH: 21
```

<212> TYPE: DNA
<213> ORGANISM: Artificial Sequence
<220> FEATURE:
<223> OTHER INFORMATION: Synthetic DNA

<400> SEQUENCE: 5
aaatgcgcaa aagatatgcg c                                              21

<210> SEQ ID NO 6
<211> LENGTH: 39
<212> TYPE: DNA
<213> ORGANISM: Artificial Sequence
<220> FEATURE:
<223> OTHER INFORMATION: Synthetic DNA

<400> SEQUENCE: 6
ctaatgggtg ctttagttgc tgataccgac gataatgcc                           39

<210> SEQ ID NO 7
<211> LENGTH: 37
<212> TYPE: DNA
<213> ORGANISM: Artificial Sequence
<220> FEATURE:
<223> OTHER INFORMATION: Synthetic DNA

<400> SEQUENCE: 7
ctgccccgtt agttgaagag actgccctcc ttttcgg                             37

<210> SEQ ID NO 8
<211> LENGTH: 24
<212> TYPE: DNA
<213> ORGANISM: Artificial Sequence
<220> FEATURE:
<223> OTHER INFORMATION: Synthetic DNA

<400> SEQUENCE: 8
cgcaaactca taaaaatcat attt                                           24

<210> SEQ ID NO 9
<211> LENGTH: 26
<212> TYPE: DNA
<213> ORGANISM: Artificial Sequence
<220> FEATURE:
<223> OTHER INFORMATION: Synthetic DNA

<400> SEQUENCE: 9
caactaaagc acccattagt tcaaca                                         26

<210> SEQ ID NO 10
<211> LENGTH: 27
<212> TYPE: DNA
<213> ORGANISM: Artificial Sequence
<220> FEATURE:
<223> OTHER INFORMATION: Synthetic DNA

<400> SEQUENCE: 10
cttcaactaa cggggcaggt tagtgac                                        27

<210> SEQ ID NO 11
<211> LENGTH: 29
<212> TYPE: DNA
<213> ORGANISM: Artificial Sequence
<220> FEATURE:
<223> OTHER INFORMATION: Synthetic DNA

<400> SEQUENCE: 11

-continued

```
cagatgatat ggtgaaaaaa tcaaatccg                                        29

<210> SEQ ID NO 12
<211> LENGTH: 38
<212> TYPE: DNA
<213> ORGANISM: Artificial Sequence
<220> FEATURE:
<223> OTHER INFORMATION: Synthetic DNA

<400> SEQUENCE: 12
gttatccgct cacaattccg agctgcatat cagatccc                              38

<210> SEQ ID NO 13
<211> LENGTH: 38
<212> TYPE: DNA
<213> ORGANISM: Artificial Sequence
<220> FEATURE:
<223> OTHER INFORMATION: Synthetic DNA

<400> SEQUENCE: 13
cgtcgtgact gggaaaactg ttgattacaa agaggcag                              38

<210> SEQ ID NO 14
<211> LENGTH: 31
<212> TYPE: DNA
<213> ORGANISM: Artificial Sequence
<220> FEATURE:
<223> OTHER INFORMATION: Synthetic DNA

<400> SEQUENCE: 14
ccatcggcca aatataagac acagccaacg c                                     31

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
gaattgtgag cggataac                                                    18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA

<400> SEQUENCE: 16
gttttcccag tcacgacg                                                    18

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
ataatgcccg cttcccaacc                                                  20

<210> SEQ ID NO 18
<211> LENGTH: 38
<212> TYPE: DNA
<213> ORGANISM: Artificial Sequence
```

```
<220> FEATURE:
<223> OTHER INFORMATION: Synthetic DNA

<400> SEQUENCE: 18
gttatccgct cacaattccg atcctcagct cctttgtc                             38

<210> SEQ ID NO 19
<211> LENGTH: 38
<212> TYPE: DNA
<213> ORGANISM: Artificial Sequence
<220> FEATURE:
<223> OTHER INFORMATION: Synthetic DNA

<400> SEQUENCE: 19
cgtcgtgact gggaaaactc atctgatacc gattaacc                             38

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
caactgaatc cgaaggaatg                                                 20

<210> SEQ ID NO 21
<211> LENGTH: 2343
<212> TYPE: DNA
<213> ORGANISM: Bacillus sp. pHSP-K38
<220> FEATURE:
<221> NAME/KEY: CDS
<222> LOCATION: (580)..(2067)
<220> FEATURE:
<221> NAME/KEY: sig_peptide
<222> LOCATION: (580)..(627)

<400> SEQUENCE: 21
agatctagca ggatttgccg atgcaaccgg cttatattta gagggaattt cttttttaaat    60 tgaatacgga ataaaatcag gtaaacaggt cctgatttta ttttttttgaa ttttttttgag   120 aactaaagat tgaaatagaa gtagaagaca acggacataa gaaaattgta ttagttttaa    180
ttatagaaaa cgcttttcta taattattta tacctagaac gaaaatactg tttcgaaagc    240
ggtttactat aaaaccttat attccggctc ttttttttaaa caggggggtga aaattcactc   300 tagtattcta atttcaacat gctataataa atttgtaaga cgcaatatac atcttttttt    360
tatgatattt gtaagcggtt aaccttgtgc tatatgccga tttaggaagg gggtagattg    420
agtcaagtag tcataattta gataacttat aagttgttga gaagcaggag agaatctggg    480
ttactcacaa gttttttaaa acattatcga aagcactttc ggttatgctt atgaatttag    540
ctatttgatt caattacttt aataatttta ggaggtaat atg atg tta aga aag       594
                                            Met Met Leu Arg Lys
                                            1               5 aaa aca aag cag ttg ggt cga cca gca caa gcc gat gga ttg aac ggt      642
Lys Thr Lys Gln Leu Gly Arg Pro Ala Gln Ala Asp Gly Leu Asn Gly
        10                  15                  20 acg atg atg cag tat tat gag tgg cat ttg gaa aac gac ggg cag cat      690
Thr Met Met Gln Tyr Tyr Glu Trp His Leu Glu Asn Asp Gly Gln His
25                  30                  35 tgg aat cgg ttg cac gat gat gcc gca gct ttg agt gat gct ggt att      738
Trp Asn Arg Leu His Asp Asp Ala Ala Ala Leu Ser Asp Ala Gly Ile
    40                  45                  50
```

```
aca gct att tgg att ccg cca gcc tac aaa ggt aat agt cag gcg gat      786
Thr Ala Ile Trp Ile Pro Pro Ala Tyr Lys Gly Asn Ser Gln Ala Asp
 55                  60                  65 gtt ggg tac ggt gca tac gat ctt tat gat tta gga gag ttc aat caa      834
Val Gly Tyr Gly Ala Tyr Asp Leu Tyr Asp Leu Gly Glu Phe Asn Gln
 70                  75                  80                  85 aag ggt act gtt cga acg aaa tac gga act aag gca cag ctt gaa cga      882
Lys Gly Thr Val Arg Thr Lys Tyr Gly Thr Lys Ala Gln Leu Glu Arg
 90                  95                 100 gct att ggg tcc ctt aaa tct aat gat atc aat gta tac gga gat gtc      930
Ala Ile Gly Ser Leu Lys Ser Asn Asp Ile Asn Val Tyr Gly Asp Val
            105                 110                 115 gtg atg aat cat aaa atg gga gct gat ttt acg gag gca gtg caa gct      978
Val Met Asn His Lys Met Gly Ala Asp Phe Thr Glu Ala Val Gln Ala
    120                 125                 130 gtt caa gta aat cca acg aat cgt tgg cag gat att tca ggt gcc tac     1026
Val Gln Val Asn Pro Thr Asn Arg Trp Gln Asp Ile Ser Gly Ala Tyr
135                 140                 145 acg att gat gcg tgg acg ggt ttc gac ttt tca ggg cgt aac aac gcc     1074
Thr Ile Asp Ala Trp Thr Gly Phe Asp Phe Ser Gly Arg Asn Asn Ala
150                 155                 160                 165 tat tca gat ttt aag tgg aga tgg ttc cat ttt aat ggt gtt gac tgg     1122
Tyr Ser Asp Phe Lys Trp Arg Trp Phe His Phe Asn Gly Val Asp Trp
            170                 175                 180 gat cag cgc tat caa gaa aat cat att ttc cgc ttt gca aat acg aac     1170
Asp Gln Arg Tyr Gln Glu Asn His Ile Phe Arg Phe Ala Asn Thr Asn
        185                 190                 195 tgg aac tgg cga gtg gat gaa gag aac ggt aat tat gat tac ctg tta     1218
Trp Asn Trp Arg Val Asp Glu Glu Asn Gly Asn Tyr Asp Tyr Leu Leu
200                 205                 210 gga tcg aat atc gac ttt agt cat cca gaa gta caa gat gag ttg aag     1266
Gly Ser Asn Ile Asp Phe Ser His Pro Glu Val Gln Asp Glu Leu Lys
215                 220                 225 gat tgg ggt agc tgg ttt acc gat gag tta gat ttg gat ggt tat cgt     1314
Asp Trp Gly Ser Trp Phe Thr Asp Glu Leu Asp Leu Asp Gly Tyr Arg
        230                 235                 240                 245 tta gat gct att aaa cat att cca ttc tgg tat aca tct gat tgg gtt     1362
Leu Asp Ala Ile Lys His Ile Pro Phe Trp Tyr Thr Ser Asp Trp Val
    250                 255                 260 cgg cat cag cgc aac gaa gca gat caa gat tta ttt gtc gta ggg gaa     1410
Arg His Gln Arg Asn Glu Ala Asp Gln Asp Leu Phe Val Val Gly Glu
265                 270                 275 tat tgg aag gat gac gta ggt gct ctc gaa ttt tat tta gat gaa atg     1458
Tyr Trp Lys Asp Asp Val Gly Ala Leu Glu Phe Tyr Leu Asp Glu Met
280                 285                 290 aat tgg gag atg tct cta ttc gat gtt cca ctt aat tat aat ttt tac     1506
Asn Trp Glu Met Ser Leu Phe Asp Val Pro Leu Asn Tyr Asn Phe Tyr
295                 300                 305 cgg gct tca caa caa ggt gga agc tat gat atg cgt aat att tta cga     1554
Arg Ala Ser Gln Gln Gly Gly Ser Tyr Asp Met Arg Asn Ile Leu Arg
        310                 315                 320                 325 gga tct tta gta gaa gcg cat ccg atg cat gca gtt acg ttt gtt gat     1602
Gly Ser Leu Val Glu Ala His Pro Met His Ala Val Thr Phe Val Asp
    330                 335                 340 aat cat gat act cag cca ggg gag tca tta gag tca tgg gtt gct gat     1650
Asn His Asp Thr Gln Pro Gly Glu Ser Leu Glu Ser Trp Val Ala Asp
345                 350                 355 tgg ttt aag cca ctt gct tat gcg aca att ttg acg cgt gaa ggt ggt     1698
Trp Phe Lys Pro Leu Ala Tyr Ala Thr Ile Leu Thr Arg Glu Gly Gly
```

```
tat cca aat gta ttt tac ggt gat tac tat ggg att cct aac gat aac    1746
Tyr Pro Asn Val Phe Tyr Gly Asp Tyr Tyr Gly Ile Pro Asn Asp Asn
375             380                 385 att tca gct aaa aaa gat atg att gat gag ctg ctt gat gca cgt caa    1794
Ile Ser Ala Lys Lys Asp Met Ile Asp Glu Leu Leu Asp Ala Arg Gln
390             395                 400                 405 aat tac gca tat ggc acg cag cat gac tat ttt gat cat tgg gat gtt    1842
Asn Tyr Ala Tyr Gly Thr Gln His Asp Tyr Phe Asp His Trp Asp Val
410             415                 420 gta gga tgg act agg gaa gga tct tcc tcc aga cct aat tca ggc ctt    1890
Val Gly Trp Thr Arg Glu Gly Ser Ser Ser Arg Pro Asn Ser Gly Leu
425             430                 435 gcg act att atg tcg aat gga cct ggt ggt tcc aag tgg atg tat gta    1938
Ala Thr Ile Met Ser Asn Gly Pro Gly Gly Ser Lys Trp Met Tyr Val
440             445                 450 gga cgt cag aat gca gga caa aca tgg aca gat tta act ggt aat aac    1986
Gly Arg Gln Asn Ala Gly Gln Thr Trp Thr Asp Leu Thr Gly Asn Asn
455             460                 465 gga gcg tcc gtt aca att aat ggc gat gga tgg ggc gaa ttc ttt acg    2034
Gly Ala Ser Val Thr Ile Asn Gly Asp Gly Trp Gly Glu Phe Phe Thr
470             475                 480                 485 aat gga gga tct gta tcc gtg tac gtg aac caa taacaaaaag ccttgagaag  2087
Asn Gly Gly Ser Val Ser Val Tyr Val Asn Gln
490             495 ggattcctcc taactcaag gctttcttta tgtcgcttag ctttacgctt ctacgacttt   2147
gaagcttggg gatccgtcga gacaaggtaa aggataaaac agcacaattc caagaaaaac   2207
acgatttaga acctaaaaag aacgaattttg aactaactca taaccgagag gtaaaaaaag  2267
aacgaagtcg agatcaggga atgagtttat aaaataaaaa aagcacctga aaggtgtct    2327 tttttttgatg tctaga                                                   2343

<210> SEQ ID NO 22
<211> LENGTH: 496
<212> TYPE: PRT
<213> ORGANISM: Bacillus sp. pHSP-K38

<400> SEQUENCE: 22

Met Met Leu Arg Lys Lys Thr Lys Gln Leu Gly Arg Pro Ala Gln Ala
1               5                   10                  15

Asp Gly Leu Asn Gly Thr Met Met Gln Tyr Tyr Glu Trp His Leu Glu
        20                  25                  30

Asn Asp Gly Gln His Trp Asn Arg Leu His Asp Ala Ala Ala Leu
    35                  40                  45

Ser Asp Ala Gly Ile Thr Ala Ile Trp Ile Pro Pro Ala Tyr Lys Gly
50              55                  60

Asn Ser Gln Ala Asp Val Gly Tyr Gly Ala Tyr Asp Leu Tyr Asp Leu
65                  70                  75                  80

Gly Glu Phe Asn Gln Lys Gly Thr Val Arg Thr Lys Tyr Gly Thr Lys
            85                  90                  95

Ala Gln Leu Glu Arg Ala Ile Gly Ser Leu Lys Ser Asn Asp Ile Asn
        100                 105                 110

Val Tyr Gly Asp Val Val Met Asn His Lys Met Gly Ala Asp Phe Thr
    115                 120                 125

Glu Ala Val Gln Ala Val Gln Val Asn Pro Thr Asn Arg Trp Gln Asp
130                 135                 140
```

-continued

```
Ile Ser Gly Ala Tyr Thr Ile Asp Ala Trp Thr Gly Phe Asp Phe Ser
145                 150                 155                 160

Gly Arg Asn Asn Ala Tyr Ser Asp Phe Lys Trp Arg Trp Phe His Phe
165                 170                 175

Asn Gly Val Asp Trp Asp Gln Arg Tyr Gln Glu Asn His Ile Phe Arg
            180                 185                 190

Phe Ala Asn Thr Asn Trp Asn Trp Arg Val Asp Glu Glu Asn Gly Asn
195                 200                 205

Tyr Asp Tyr Leu Leu Gly Ser Asn Ile Asp Phe Ser His Pro Glu Val
210                 215                 220

Gln Asp Glu Leu Lys Asp Trp Gly Ser Trp Phe Thr Asp Glu Leu Asp
225                 230                 235                 240

Leu Asp Gly Tyr Arg Leu Asp Ala Ile Lys His Ile Pro Phe Trp Tyr
245                 250                 255

Thr Ser Asp Trp Val Arg His Gln Arg Asn Glu Ala Asp Gln Asp Leu
260                 265                 270

Phe Val Val Gly Glu Tyr Trp Lys Asp Val Gly Ala Leu Glu Phe
275                 280                 285

Tyr Leu Asp Glu Met Asn Trp Glu Met Ser Leu Phe Asp Val Pro Leu
290                 295                 300

Asn Tyr Asn Phe Tyr Arg Ala Ser Gln Gln Gly Gly Ser Tyr Asp Met
305                 310                 315                 320

Arg Asn Ile Leu Arg Gly Ser Leu Val Glu Ala His Pro Met His Ala
325                 330                 335

Val Thr Phe Val Asp Asn His Asp Thr Gln Pro Gly Glu Ser Leu Glu
340                 345                 350

Ser Trp Val Ala Asp Trp Phe Lys Pro Leu Ala Tyr Ala Thr Ile Leu
355                 360                 365

Thr Arg Glu Gly Gly Tyr Pro Asn Val Phe Tyr Gly Asp Tyr Tyr Gly
370                 375                 380

Ile Pro Asn Asp Asn Ile Ser Ala Lys Lys Asp Met Ile Asp Glu Leu
385                 390                 395                 400

Leu Asp Ala Arg Gln Asn Tyr Ala Tyr Gly Thr Gln His Asp Tyr Phe
405                 410                 415

Asp His Trp Asp Val Val Gly Trp Thr Arg Glu Gly Ser Ser Ser Arg
420                 425                 430

Pro Asn Ser Gly Leu Ala Thr Ile Met Ser Asn Gly Pro Gly Gly Ser
435                 440                 445

Lys Trp Met Tyr Val Gly Arg Gln Asn Ala Gly Gln Thr Trp Thr Asp
450                 455                 460

Leu Thr Gly Asn Asn Gly Ala Ser Val Thr Ile Asn Gly Asp Gly Trp
465                 470                 475                 480

Gly Glu Phe Phe Thr Asn Gly Gly Ser Val Ser Val Tyr Val Asn Gln
485                 490                 495
```